United States Patent [19]

Oldendorf et al.

[11] Patent Number: 4,889,201

[45] Date of Patent: Dec. 26, 1989

[54] DRYING BALANCE WITH EVALUATION CIRCUIT FOR DETERMINING THE END OF THE DRYING

[75] Inventors: Christian Oldendorf, Göttingen; Günther Maaz, Uslar; Klaus Nottbohm, Sandhausen; Volker Handwerk, Grünstadt, all of Fed. Rep. of Germany

[73] Assignee: Sartorius GmbH, Fed. Rep. of Germany

[21] Appl. No.: 300,898

[22] Filed: Jan. 24, 1989

[30] Foreign Application Priority Data

Jan. 25, 1988 [DE] Fed. Rep. of Germany ....... 3802006

[51] Int. Cl.$^4$ ................ G01G 19/40; G01G 23/00; G01N 25/56
[52] U.S. Cl. ................... 177/25.14; 177/245; 73/73; 364/568
[58] Field of Search ................. 177/25.14, 245; 73/73; 364/567, 568

[56] References Cited

U.S. PATENT DOCUMENTS

| | | | |
|---|---|---|---|
| 4,131,011 | 12/1978 | Ling | 73/863.61 X |
| 4,165,633 | 8/1979 | Raisanen | 177/25.14 X |
| 4,168,623 | 9/1979 | Thomas, Jr. | 177/25.14 X |
| 4,316,384 | 2/1982 | Pommer et al. | 364/567 X |
| 4,750,143 | 6/1988 | Heitz et al. | 177/25.13 X |

Primary Examiner—George H. Miller, Jr.
Attorney, Agent, or Firm—Eric P. Schellin

[57] ABSTRACT

A drying balance is disclosed with a means (11) for supplying energy for the drying of material to be weighed located on the balance scale (6,16) and with a digital evaluating unit (23,24,25) for calculating the moisture content from the measured weight loss of the specimen and for determining the end point of the drying in which balance the digital evaluating unit (23,24,25) calculates the inflection point from the chronological course of the weight loss and derives the criterion for determining the final point therefrom. The criterion for the final point consists in that the slope of the drying curve drops below a certain value which is derived from the coordinates or the slope of the drying curve at the inflection point.

9 Claims, 7 Drawing Sheets

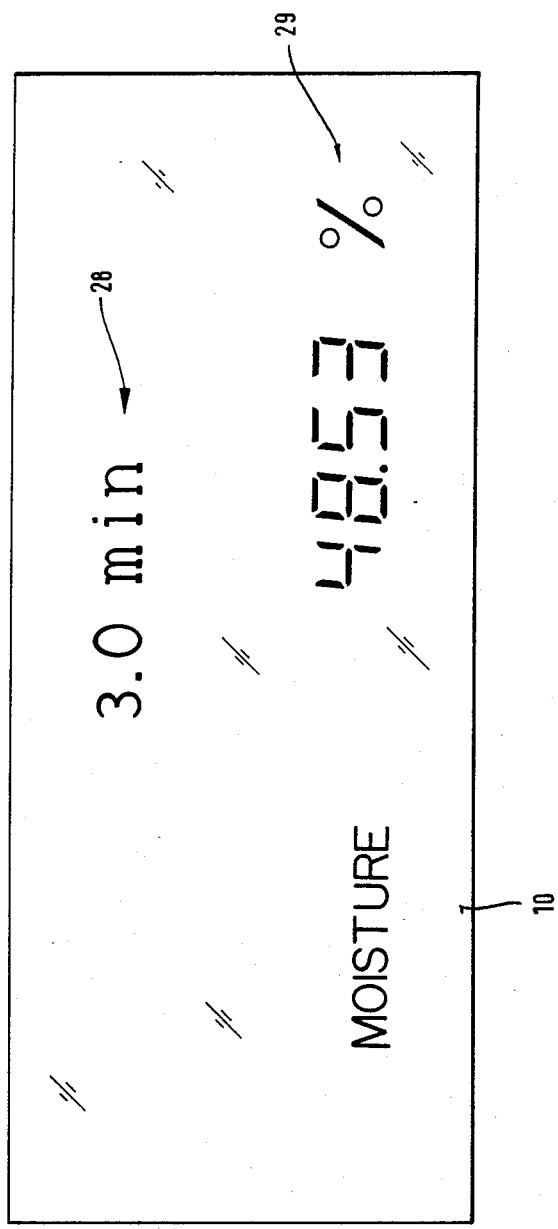

DRYING BALANCE WITH EVALUATION CIRCUIT FOR DETERMINING THE END OF THE DRYING

BACKGROUND OF THE INVENTION

The invention relates to a drying balance with means for supplying energy for the drying of material to be weighed located on the balance scale and with a digital evaluating unit for calculating the moisture content from the measured weight loss of the specimen and for determining the end point of the drying step.

PRIOR ART

The mechanical design of drying balances of this type is described e.g. in U.S. Pat. No. 4,666,007.

The drying time must frequently be set in a fixed manner by the user. As a result thereof, variations of the individual specimens in their drying behavior can not be considered, for which reason the times to be set must be increased by considerable additional safety increments, i.e. over compensated, so that the dryings generally last an unnecessarily long time.

In addition to the above, DE-OS No. 32 31 004 teaches the calculation of the chronological weight gradient of the drying curve and the termination of the drying as soon as this gradient drops below a set limit value. DE-OS No. 32 31 004 suggests for the magnitude of this set limit value only that the limit value be made equal to the dispersion of the measured points. As a result, this limit is relatively greater in the case of small specimens and in the same manner the limit value is likewise greater in the case of unsteady environmental conditions of the drying balance, so that the reproducibility of the measurements suffers. In general, the setting of a fixed value for the weight gradient as criterion for the end point of the drying can consider the individual drying properties only in an inadequate fashion.

Furthermore, Japanese patent application No. 60-23 00 36 (Patent Abstracts of Japan p-446, Apr. 15, 1986, vol. 10, No. 97) teaches the determining of the point in time of a limiting moisture content, e.g. by means of the rise of the specimen temperature, and he calculating of the moisture content of the specimen from the measured data at this point in time. However, this assumes the measuring of the specimen temperature, which is difficult in drying balances.

Finally, U.S. Pat. No. 4,165,633 teaches the calculation of estimated values for the final result of the drying from the course of the drying curve without describing details of the calculation of estimated values. That point in time is then defined as the end point at which two successive estimated values differ from one another by less than 1%. However, there is the danger in this method that two (or even more) successive estimated values can coincide as a result of coincidental variations without the end of the weight loss having actually been reached already. This results in the danger that the drying is terminated too early.

BRIEF DESCRIPTION OF THE INVENTION

The invention therefore has the problem of creating a drying balance which more heavily takes into consideration the drying behavior of the individual specimen and therefore permits a clear reduction of the time until there is obtained information of a reliable drying result.

The invention achieves this as follows: The digital evaluation unit calculates the inflection point or from the chronological course of the weight loss i.e. drying curve, and derives the criterion for determining the end point therefrom.

In a first advantageous development the digital evaluating unit calculates to tis end the weight loss $\Delta m_c$ of the specimen until the inflection point and defines as end point of the drying the point on the drying curve at which the weight loss of the specimen drops below a set fraction of $\Delta m_c$ per time unit. In a second advantageous development the digital evaluating unit calculates the slope of the drying curve at the inflection point and defines as final point of the drying the point on the drying curve at which the instantaneous slope drops below a set fraction of this slope at the inflection point. In a third advantageous development the digital evaluating unit calculates the quotient $\Delta m_c/t_c$, in which $t_c$ is the drying time until the inflection point is reached and $\Delta m_c$ the weight loss of the specimen at the inflection point; then, the final point of the drying is defined as the point on the drying curve at which the instantaneous slope drops below a set fraction of the quotient $\Delta m_c/t_c$.

In an advantageous further development not only the inflection point is calculated by the digital evaluating unit and the criterion for the final point of the drying determined therefrom but also in addition the point of greatest curvature following the inflection point is calculated. After this point of greatest curvature, the drying curve generally obeys quite well an exponential function like that described e.g. in:

(1) Title: "Automatic Microwave Moisture Meter"; authors: Charles E. Thomas, Manuel C. Bourlas, Tibor S. Laszlo, Donald F. Magin: 14th Microwave Power, Symposium 1979, pp. 150–152; Monaco, June 11–15, 1979.

(2) Title: "Feuchtebestimmung mit IR-Trocknungsgerat" (Moisture Determination with IR-Drying Device); authors: Dr. Volker Handwerk, Dr. Gunther Maaz; Zeitschrift fur Lebensmitteltechnologie und -verfahrenstechnik, vol. 6, 1987, pp. 522–526, Huthig-Verlag, Heidelberg.

The digital evaluating unit can therefore derive an estimated value for the final weight after this point of greatest curvature from several points with great reliability. The digital evaluating unit advantageously outputs this estimated value as final weight when the final point of the drying is reached; a continuous output or an output upon request of the operator is advantageously possible.

In another advantageous further development the digital evaluating unit also calculates in addition to the estimated value for the dry weight an estimated value for the end point in time and outputs as a derivative thereof the time still required until the final point of the drying either continuously or upon request of the operator. In this manner the operator can obtain early information about the measuring time probably still required.

The digital evaluating device advantageously updates the estimated values for the dry weight and the end point in time in a continuous manner until the final point of the drying step.

BRIEF DESCRIPTION OF THE DRAWINGS

The invention is described in the following with reference made to the figures.

FIG. 7 shows the display field of a drying balance with display of the measuring time still required.

Figure 1:
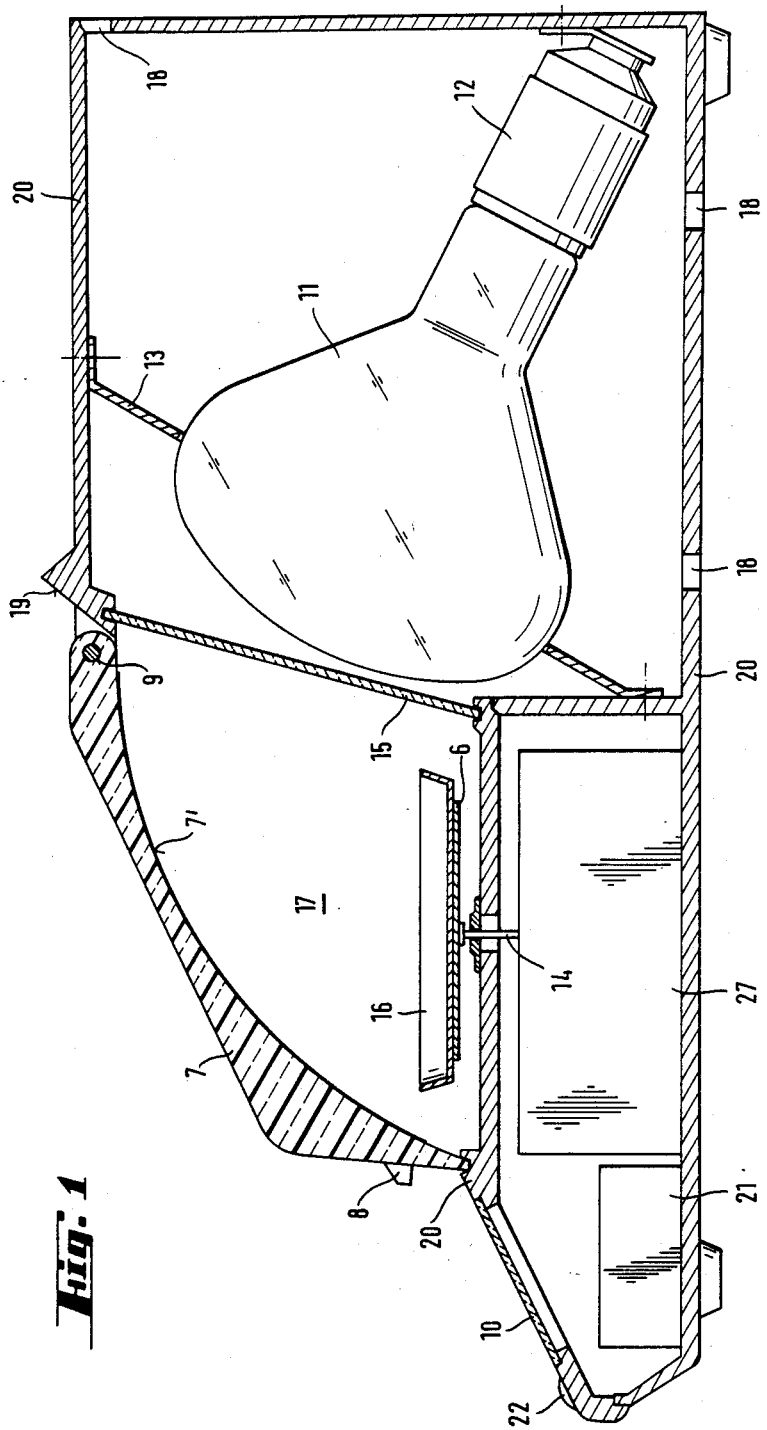
FIG. 1 shows the mechanical design of the drying balance in section.

The drying balance shown in FIG. 1 consists of a multipartite housing 20 in which weighing system 27 is housed. The type of this weighing system is not significant for the invention; It can be e.g. an electronic system in accordance with the principle of the electromagnetic compensation of force. A lower scale 6 is connected to weighing system 27 via force introduction member 14. Balance scale 16 with the specimen to be dried and weighed rests in a removable manner on lower scale 6. Furthermore, display 10 is integrated in housing 20. Infrared light 11 is shown as an example of a component for supplying energy for the drying and is located behind balance scale 16 nd weighing system 27. Infrared light 11 is fixed to housing 20 by socket 12 and by sleeve 13. Infrared light 11 is arranged in such a manner that the direction of its main beam forms an angle of approximately 10°-40° to the horizontal. The chamber of the infrared light is sealed from weighing chamber 17 by wall 15 which is permeable to heat radiation but not to air currents. The ventilation and cooling of infrared light 11 is assured by perforations 18 in the bottom and the back of housing 20.

Furthermore, the drying balance comprises a cover 7 which is manufactured e.g. from a plastic and comprises a reflecting coating on its inner side 7'. This reflecting inner surface reflects the light of infrared light 11 in a closed state and directs it in a concentrated manner onto a specimen to be dried in balance scale 16. Cover 7 comprises through perforation 9 on its upper, rear end through which perforation a shaft fixed to the housing extends. In this manner, cover 7 is rotatably mounted at this end; when opened, it comes to rest against stop 19 on the housing.

Handle 8 is used to grasp the cover during opening and closing.

Finally, FIG. 1 schematically indicates the electronic circuitry 21 and operating key 22.

Figure 2:
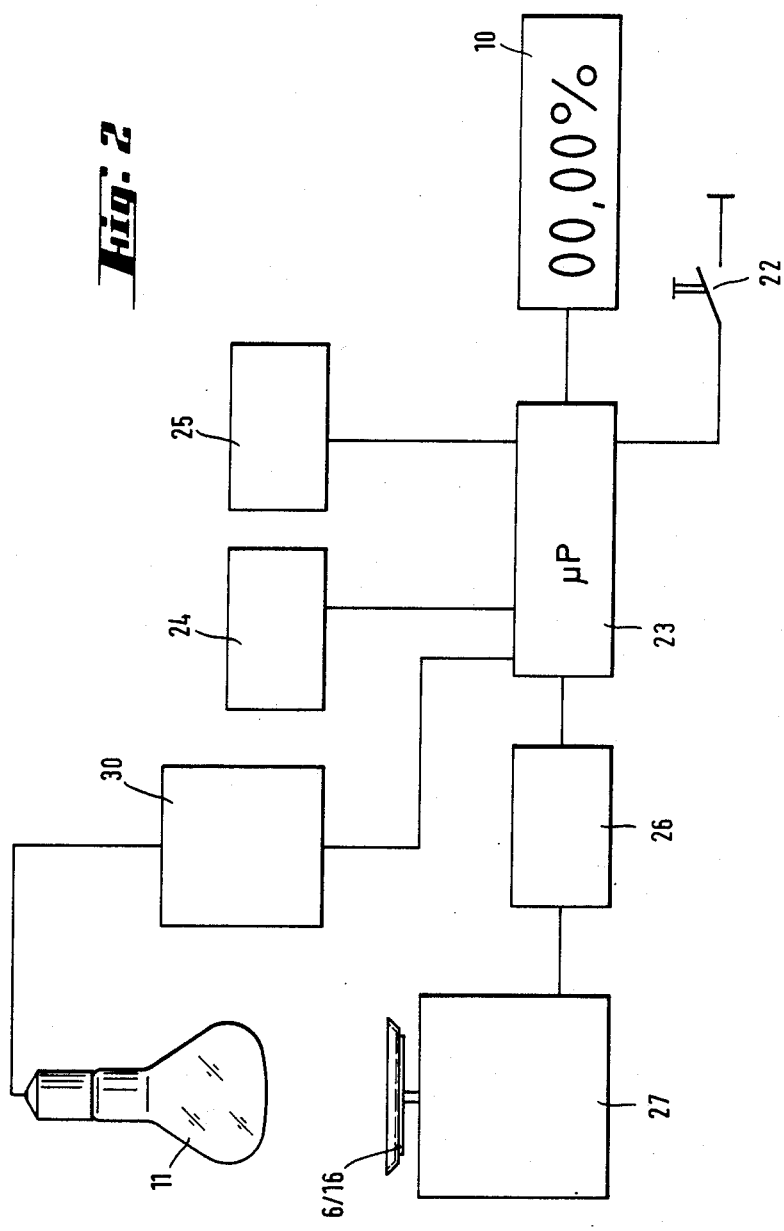
FIG. 2 shows a block diagram of the electronic circuitry of the drying balance.

This electronic circuitry is shown in FIG. 2 again in more detail. The signal of weighing system 27 passes through preprocessing stage 26, which can consist e.g. of an analog-digital converter and an analog and/or digital filter. The weight signal then passes to digital evaluating unit 23, 24, 25 which consists e.g. of microprocessor 23, program memory 24 and main memory 25 for the temporary storage of measured values, etc. The digital evaluating unit then supplies display 10; in addition, a digital output can be provided. Program emory 24 contains the actual evaluating program and the program for determining the final point of the drying, as will be described in the following with reference made to FIGS. 3 to 6. The digital evaluating unit also controls power electronics 30 for infrared light 11.

Figure 3:
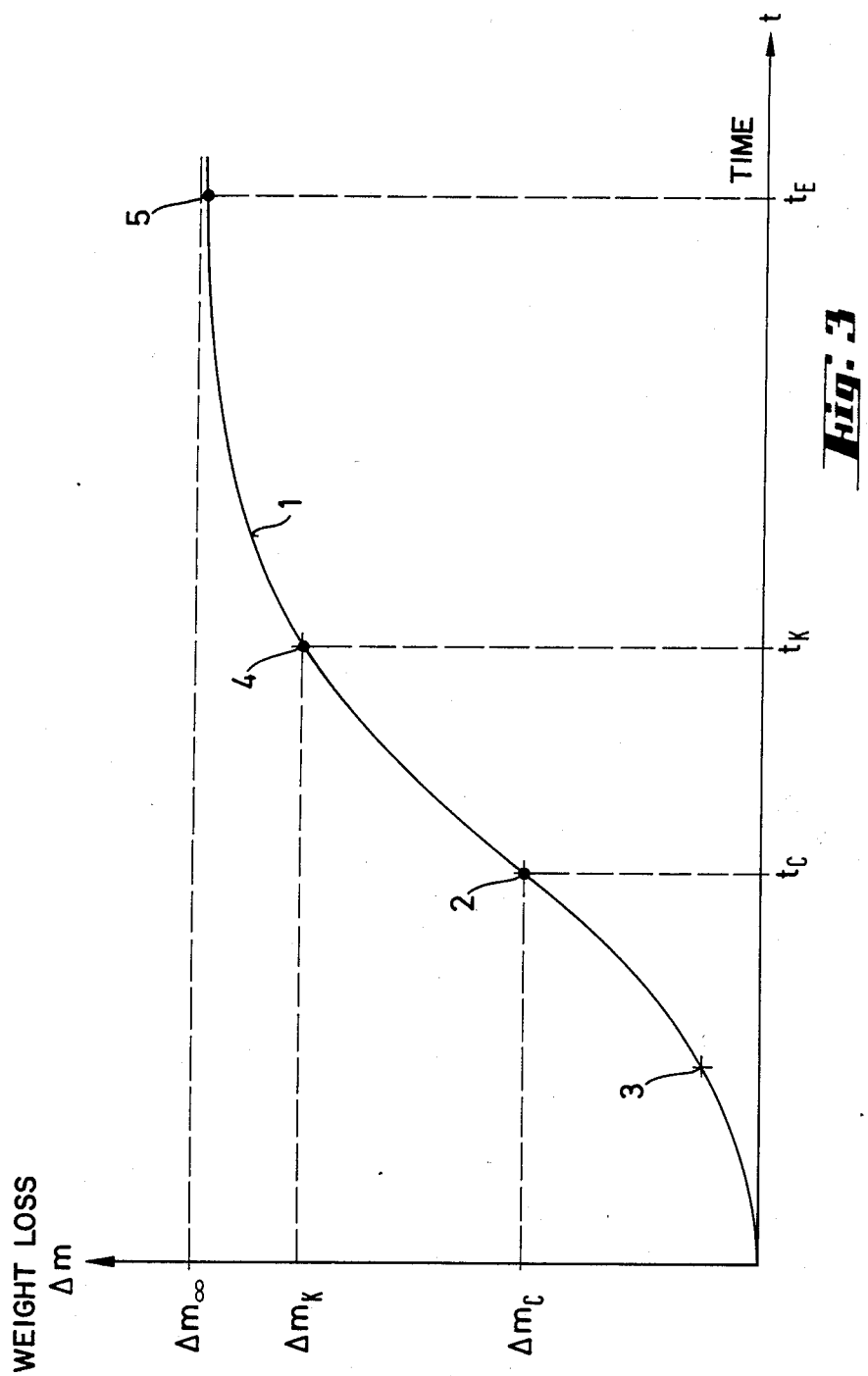
FIG. 3 shows a drying curve with three characteristic points.

FIG. 3 shows the chronological course of the weight loss m of a specimen during the drying process by way of example. This drying curve 1 starts at time t=0 with $\Delta m=0$ and sytotically reaches a value $\Delta m_c$ for the weight loss at large time values. Drying curve 1 exhibits inflection point 2 therebetween at which the slope of the drying curve is the greatest. The time associated with inflection point 2 is $t_c$ and the weight loss associated with inflection point 2 is $\Delta m_c$. Inflection point 2 is not only the point with the greatest slope of drying curve 1 but it also separates the two areas of differing curvature from one another. In area $t<t_c$ point 3 represents the point of sharpest curvature of drying curve 1. In the area $t>t_c$ point 4 represents the point of sharpest curvature (but in the opposite direction of curvature) of drying curve 1. The time associated with point 4 is t and the associated weight loss is $\Delta m_k$.

Figure 4:
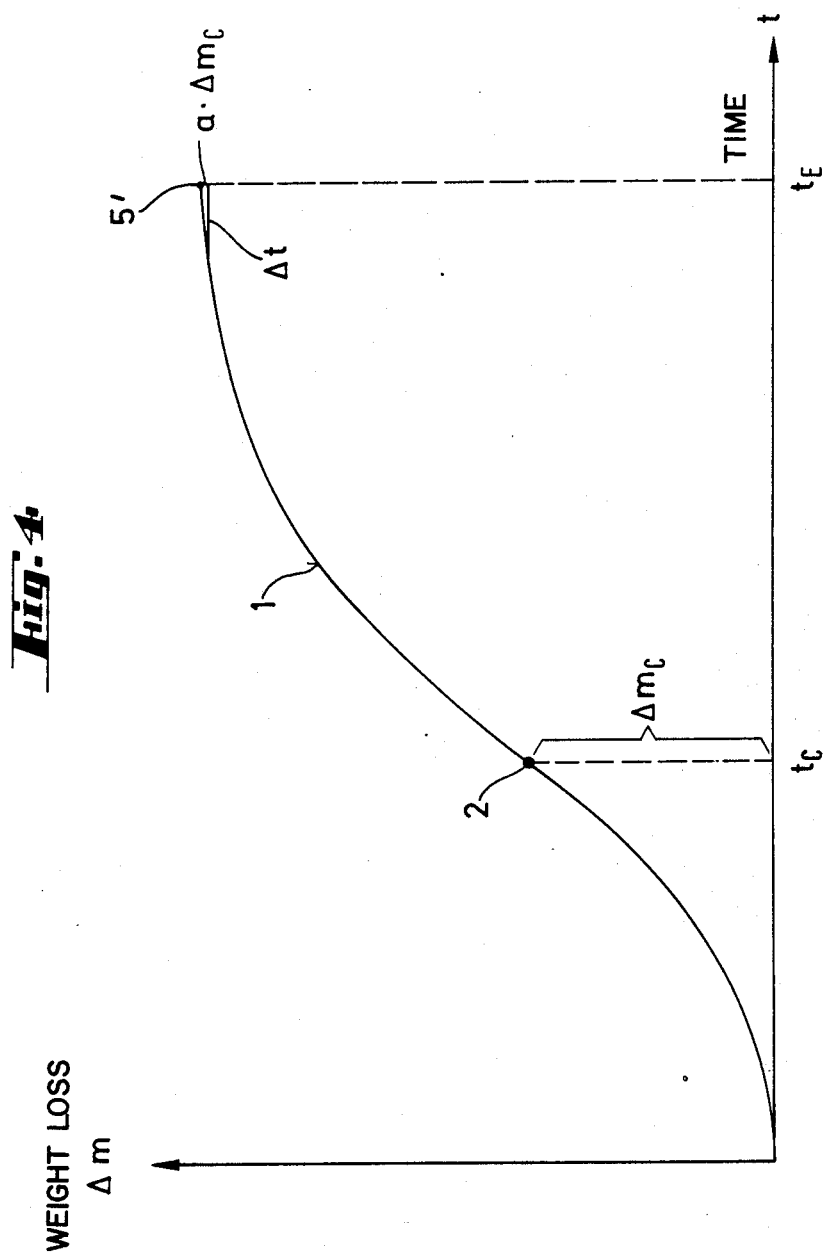
FIG. 4 shows the drying curve with the determination of the final point according to a first method.
Figure 5:
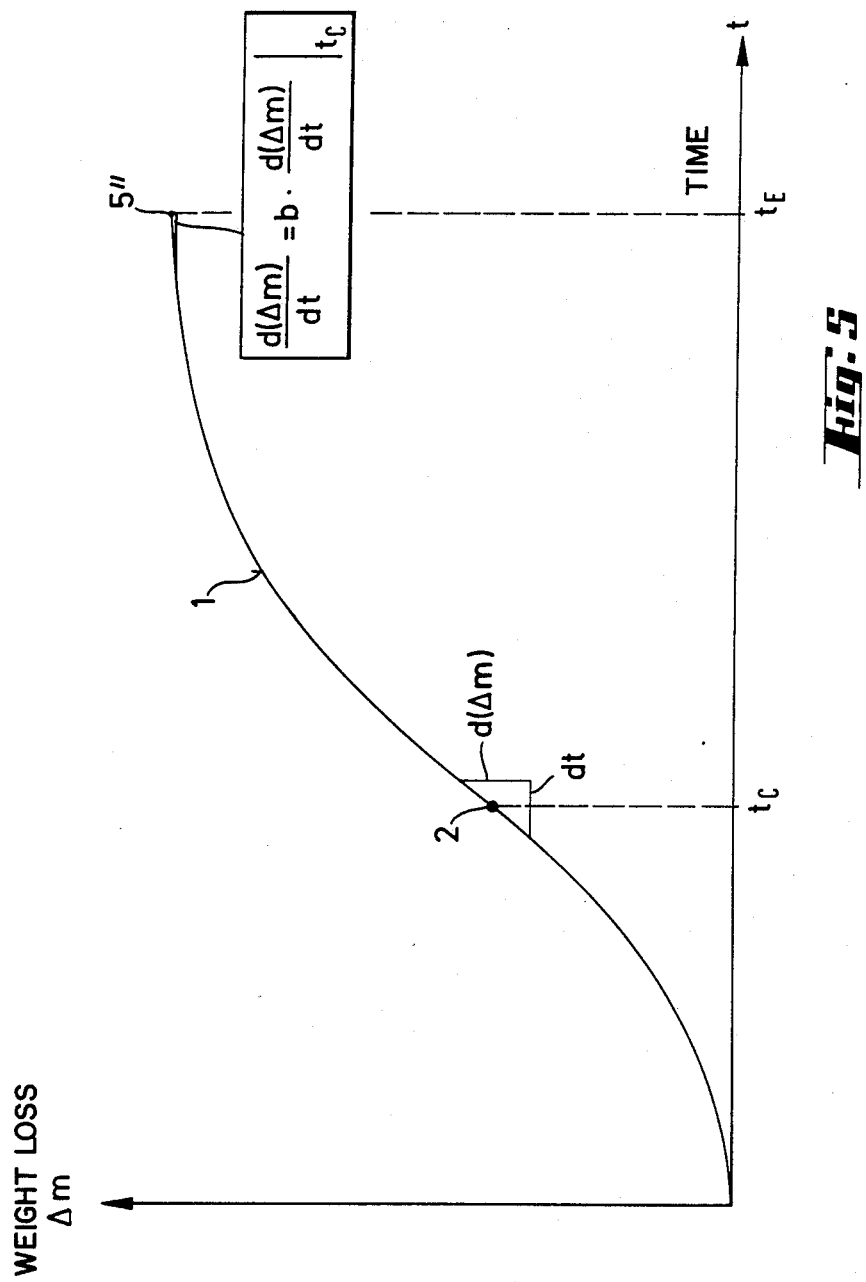
FIG. 5 shows the drying curve with the determination of the final point according to a second method.
Figure 6:
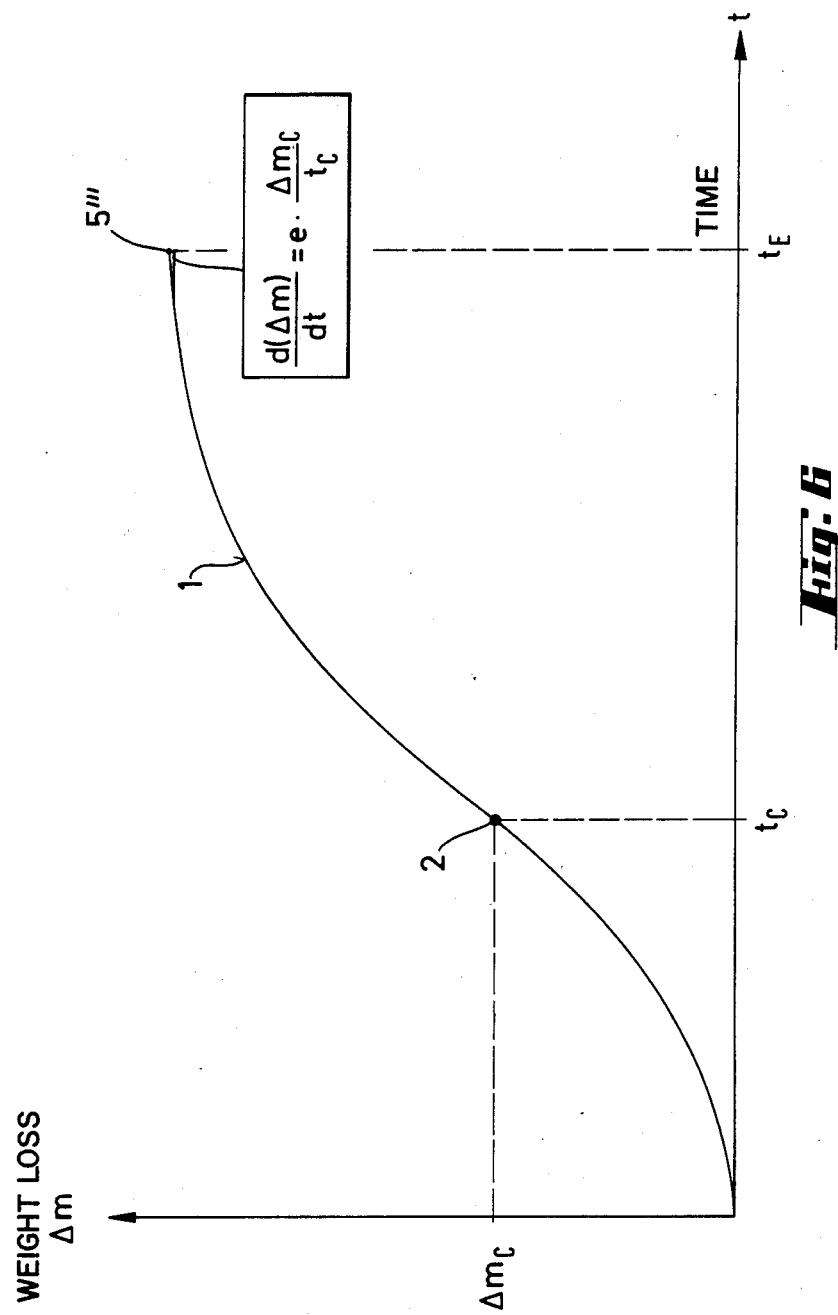
FIG. 6 shows the drying curve with the determination of the final point according to a third method.

Since the "actual" end of the drying process is reached only asymptotically, the real end of the drying process is defined as point 5 on drying curve 1 at which point the final value $\Delta m_\infty$ has been reached within a set range of exactitude or at which the final value m can be mathematically estimated within a set range of exactitude. In FIGS. 4 to 6, three different possibilities for the determination of the criterion for the final point utilizing inflection point 2 are explained.

In FIG. 4 the weight loss $\Delta m_c$ is determined at inflection point 2 of drying curve 1. The final point is then defined as point 5', at which the slope of drying curve is smaller or equal to a set fraction of $\Delta m_c$. This, in equation form:

$$\frac{d(\Delta m)}{dt} \leq \frac{a}{\Delta t} \cdot \Delta m_c$$

The end point is determined in this instance by the selection of constant "a" and of time unit t (e.g. the time between two successive measuring cycles). Of course, a general determination can also be made that the following is valid:

$$\frac{d(\Delta m)}{dt} \leq f \cdot \frac{\Delta m_c}{\Delta t}$$

In FIG. 5 the slope $d(\Delta m)/dt$ of drying curve 1 is determined at inflection point 2. Th final point is then defined as point 5", at which the slope of drying curve 1 is smaller than or equal to a set fraction "b" of the slope at inflection point 2. Thus, in equation form:

$$\frac{d(\Delta m)}{dt} \leq b \cdot \frac{d(\Delta m)}{dt} t_c$$

In this instance the final point is determined by the selection of constant b.

In FIG. 6 quotient $\Delta m_c/t_c$ is formed at inflection point 2 of drying curve 1. The final point is then defined to be 5''', at which the slope of drying curve is smaller than or equal to a set fraction "e" of this quotient. Thus, in equation form:

$$\frac{d(\Delta m)}{dt} \leq e \cdot \frac{\Delta m_c}{t_c}$$

The final point is determined in this instance by the selection of constant :e".

In FIGS. 4 to 6, constants "a", "b" and "e" have been selected so as to be relatively large with approximately 0.1 in order to still be able to graphically show the slope of the drying curve at end points 5', 5" and 5'''. This corresponds to a very rapid moisture-content measurement of average exactitude. Naturally, larger, or in particular smaller values are also possible for the constants. The determination of the slope $d(\Delta m)/dt$ of the drying curve is mathematically most simply performed in an approximate manner by forming the difference of successive measuring points on the drying curve in a set time. This is mathematically exactly the slope of the chord between the two measured points, but reproduces sufficiently exactly the slope of the curve (—slope of the tangent).

Of course, customary mathematical forms can also be used to smooth the individual measured points on the drying curve or it can be required that the criterion for the final point must be met several times in succession (e.g. over a time period of 10 sec.) in order to output the signal "end of drying".

Once the final point of the drying has been determined according to one of the possibilities described above, the last measured value can be outputted as the final result in the simplest case. A greater measuring exactitude (or a shorter measuring time at the same measuring exactitude results, however, if an estimated value for $\Delta m_c$ is calculated from the course of the drying curve instead and this value is outputted.

It turned out thereby that it is advantageous to start with the estimation of $\Delta m_\infty$ at the point of greatest curvature (point 4 in FIG. 3): Then, a first estimated value for $\Delta m_\infty$ can be calculated e.g. 30 sec. after time $t_k$ from coordinates $t_k$ and $\Delta m_k$ of point 4 and from the coordinates of the following points on drying curve 1. Subsequently, this estimated value can be updated e.g. every 10 sec. The first estimated values are not very exact yet; however, as the time increases, the estimation becomes more and more exact since more measured points can be evaluated and since drying curve 1 becomes flatter and flatter with time. The estimated value for $\Delta m_\infty$ and for values mathematically derived therefrom such as the moisture content $\Delta m_\infty/m_c$ ($m_c$=the initial weight of a specimen), the dry-substance content, etc. can be continuously displayed or displayed upon request of the operator. Operating key 22 is provided for this request adjacent to display 10 (FIG. 1, 2).

Just as an estimated value for the final weight $\Delta m_\infty$ can be calculated after point 4 on the drying curve, an estimated value for the final point in time $t_E$ can also be calculated. This estimated value is not very exact at first, to be sure, but it can serve as an indication to the operator of the approximate time still required for the drying. For this reason, a further display 28 is provided adjacent 29 of the moisture content calculated from the instantaneous measured value in the embodiment of display field 10 of the drying balance shown in FIG. 7, in which display 28 the approximate time needed until the display of the final result is indicated. This indication is either calculated once by the digital evaluating unit following point 4 and then continuously decremented via a clock or the final point in time of the drying is continuously estimated anew from the new measured values and this newest estimated value is displayed. When the final point of the drying has been reached, upper line 28 of display 10 in FIG. 7 goes out and the final result of the drying is displayed, perhaps with the explanation "final result" in the upper line.

We claim:

1. A drying balance with a means for supplying energy for the drying of material to be weighed located on the balance scale, with a digital evaluating unit for calculating the moisture content from the measured weight loss of the specimen and for determining the end point of the drying, characterized in that the digital evaluating unit (23,24,25) calculates the inflection point (2) from the chronological course of the weight loss (drying curve) and derives the criterion for the determination of the final point therefrom.

2. The drying balance according to claim 1, wherein the digital evaluating unit (23,24,25) calculates the weight loss $\Delta m_c$ of the specimen when the inflection point (2) is reached and terminates the drying as soon as the weight loss of the specimen drops below a set fraction of $\Delta m_c$ per unit of time.

3. The drying balance according to claim 1, wherein the digital evaluating unit (23,24,25) calculates the slope at the inflection point (2) and terminates the drying as soon as the instantaneous slope of the drying curve (1) drops below a set fraction of the slope at the inflection point.

4. The drying balance according to claim 1, wherein the digital evaluating unit (23,24,25) forms the quotient $\Delta m_c/t_c$ from the weight loss $\Delta m_c$ of the specimen when the inflection point (2) is reached and from the drying time $t_c$ until the inflection point has been reached and terminates the drying as soon as the instantaneous slope of quotient $\Delta m_c/t_c$.

5. The drying balance according to claim 1 wherein the digital evaluating unit (23,24,25) additionally calculates the point of greatest curvature (4) following the inflection point (2) and calculates an estimated value for the dry weight after this point of greatest curvature from several points on the drying curve (1).

6. The drying balance according to claim 5, wherein the digital evaluating unit (23,24,25) outputs the estimated value as final weight of the drying when the final point of the drying is reached.

7. The drying balance according to claim 5, wherein the digital evaluating unit (23,24,25) outputs the estimated value continuously or upon request of the operator.

8. The drying balance according to claim 5, wherein in addition to calculating the estimated value for the dry weight, the digital evaluating unit (23,24,25) also calculates an estimated value for the final point in time and outputs on the basis of this estimated value the time still required until the final point either continuously or upon request of the operator.

9. The drying balance according to claim 5, herein the digital evaluating unit (23,24,25) continuously updates the estimated value(s) until the end point of the drying has been reached.

* * * * *